US00PP18753P2

(12) United States Plant Patent
Bradford

(10) Patent No.: US PP18,753 P2
(45) Date of Patent: Apr. 22, 2008

(54) PEACH TREE NAMED 'SUGARPEACH III'

(50) Latin Name: *Prunus persica*
Varietal Denomination: Sugarpeach III

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,908

(22) Filed: Dec. 13, 2006

(51) Int. Cl.
*A01H 5/00* (2006.01)

(52) U.S. Cl. ..... Plt./197
(58) Field of Classification Search ..... Plt./197
See application file for complete search history.

(56) References Cited

U.S. PATENT DOCUMENTS

PP7,066 P * 12/1989 Bradford et al.
PP14,677 P2 * 4/2004 Bradford

* cited by examiner

*Primary Examiner*—Kent Bell

(57) ABSTRACT

The present invention relates to a new and distinct variety of peach tree, *Prunus persica,* broadly characterized by a large size, vigorous, hardy, self-fertile, productive and regular bearing tree. The fruit matures under the ecological conditions described in the early part of June, with first picking on Jun. 7, 2006. The fruit is uniformly large in size, sub-acidic and sweet in flavor, globose to oblate in shape, clingstone in type, firm in texture, yellow in flesh color, and fully red in skin color.

1 Drawing Sheet

Botanical classification: *Prunus persica.*
Variety denomination: 'SUGARPEACH III'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'SUGARPEACH III'.

During the spring of 1998 I gathered fruit from several different unnamed seedlings in my experimental orchard located near Le Grand, Calif., in Merced County (San Joaquin Valley). One particular group of peaches was yellow in flesh color, clingstone in type, and sub-acid in flavor, and was thus designated as "YPCSA (OP)". The seeds from this fruit were removed, cracked, stratified, germinated, and grown as seedlings on their own root in my greenhouse. Upon reaching dormancy that fall, I transplanted them to a cultivated area in the experimental orchard described above. During the fruit evaluation season of 2001 I selected the claimed variety as a single tree from the group of "YPCSA (OP)" described above. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to 'SPRING CANDY' (U.S. Plant Pat. No. 14,677) peach by producing peaches that are firm in texture, yellow in flesh color, sub-acid in flavor, and mostly red in skin color, but is distinguished therefrom by blooming later, by requiring more chilling hours, and by producing fruit that is clingstone instead of freestone in type, that is sweeter in taste, and that matures about twelve days earlier.

SUMMARY OF VARIETY

In summary, the present variety is characterized by a large size, vigorous, hardy, self-fertile, productive and regular bearing tree. The fruit matures under the ecological conditions described in the early part of June, with first picking on Jun. 7, 2006. The fruit is uniformly large in size, sub-acidic and sweet in flavor, globose to oblate in shape, clingstone in type, firm in texture, yellow in flesh color, and full red in skin color.

DRAWING

The accompanying photograph consists of four whole fruits positioned to display the characteristics of the skin color and form, one fruit divided transversely to the suture plane to reveal the flesh and stone, a clean freshly removed stone, two insets to reveal buds and a blossom, one entire leaf, and a typical tip shoot.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 12, 2006, on the original tree during its eighth growing season. All major color code designations are by reference to the Inter-Society Color Council, National Bureau of Standards. Common color names are also used occasionally.

Tree

Size: Large, reaching and maintaining a height of 11' [3.35 m.] and a spread of 10' [3.05 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximately chilling requirement: 800 hours.

Trunk:

*Size.*—Medium, reaching a maximum diameter of 5½" [140 mm.] after the eighth growing season.

*Texture.*—Shaggy.

*Dark color.*—A Brownish gray [64. brGy] and Dark brown [59. d.Br] variegation with Light yellowish brown [76. l.yBr] crevices present.

*Lenticels.*—Approximate Number Per Square Inch: 8. Color: Strong orange yellow [68. s.OY]. Typical Size: ⅛" [3.2 mm.] to 7/16" [11.1 mm.]. Shape: Eye-shaped to elongated.

Branches:

*Size.*—Diameter of limb is 3¼" [83 mm.] measured 12" above the crotch, 2⅛" [54 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Moderate yellowish brown [77. m.yBr] over a Moderate olive brown [95. m.OlBr] under color.

*Lenticels.*—Number Per Square Inch: More than 60 on second year wood. Color: Light orange yellow [70 l.OY]. Typical size: 1/64" [0.4 mm.] to 3/32" [2.4 mm.] on second year wood. Shape: Elongated.

Leaves:

*Size.*—Large. Average Length: 6½" [165 mm.]. Average Width: 1½" [38 mm.].

*Arrangement.*—Alternate.

*Thickness.*—Medium.

*Form.*—Elliptical.

*Apex.*—Acuminate.

*Base.*—Acute, with a base angle of 75 to 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ½" [12.7 mm.]. Average Thickness: 1/16" [1.6 mm.]. Color: Brilliant yellow green [116. brill.YG].

*Stipules.*—Number: Usually 2 per leaf, up to 6 per growing tip. Average Length: ¼" [6.4 mm.]. Color: Strong yellow green [117. s.YG] becoming Strong reddish brown [40. s.rBr] with maturity.

*Glands.*—Number: 2 to 4 per leaf. Position: Alternately positioned on petiole and base of blade. Size: Medium: Form: Reniform. Color: Very yellow green [115. v.YG] becoming Moderate reddish brown [43. m.rBr] with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 9/16" [14.3 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepal and petal locations alternately positioned.

*Type.*—Showy, large.

*Average flower diameter.*—1¾" [44.5 mm.].

*Number of petals.*—Usually five, extra petal fragments and double blossoms rarely occur.

*Petal shape.*—Circular to oval.

*Petal margin.*—Somewhat wavy.

*Average petal diameter.*—¾" [19.1 mm.].

*Average petal length.*—13/16" [20.6 mm.].

*Petal apex.*—Rounded.

*Petal base.*—Rounded to somewhat truncate.

*Petal color.*—Pale pink [7. p.Pk] toward the apex, Light pink [4. l.Pk] toward the base.

*Anther color.*—Dark red [16. d.R] over a Light yellow [86. l.Y] center at bloom onset.

*Stigma color.*—Light greenish yellow [101. l.gY].

*Sepal color.*—Dark purplish red [259. d.pR].

*Sepal length.*—¼" [6.4 mm.].

*Sepal width.*—3/16" [4.8 mm.].

*Average pistil length.*—13/16" [20.6 mm.].

*Average stamen length.*—⅝" [15.9 mm.].

*Fragrance.*—Moderate.

*Blooming period.*—Quite late, two days after 'Diamond Princess' (U.S. Plant Pat. No. 7,066) peach.

*Onset of bloom.*—One percent on Mar. 10, 2006.

*Date of full bloom.*—Mar. 20, 2006.

*Duration of bloom.*—One to two weeks, dependent on ambient temperature.

*Number per cluster.*—1 to 3 with single flowers most common.

FRUIT

Maturity when described: Firm ripe, Jun. 12, 2006.

Date of first picking: Jun. 7, 2006.

Date of last picking: Jun. 17, 2006.

Size: Uniform, large.

*Average diameter axially.*—2 15/16" [75 mm.].

*Average diameter across suture plane.*—3⅛" [79 mm.].

*Average diameter across cheek plane.*—3¼" [83 mm.].

*Typical weight.*—8.9 ounces [252 grams].

Form: Symmetrical, globose to oblate, typically bulging along the suture.

*Longitudinal section form.*—Oblate.

*Axial view.*—Round to elliptical.

Suture: A shallow groove in the stem cavity, an inconspicuous line along the side, and a sharper groove toward the apex ending just beyond the pistil point.
Ventral surface: Rounded, lipped toward the apex on both sides.
Lips: Equal.
Cavity: Flaring, elongated in the suture plane, suture usually showing on both sides, Strong yellow [84. s.Y] stem markings typical.
*Depth.*—7/16" [11.1 mm.].
*Breadth.*—1" [25.4 mm.].
Base: Truncate.
Apex: Rounded, cordate if viewed parallel to the suture.
Pistil point: Apical, short, often depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed.
*Color.*—Dark red [16. d.R] over a Strong red [12. s.R] background with very slight Yellowish white [92. yWhite] freckling.
Flesh:
*Color.*—Brilliant yellow [83. brill.Y] with Strong red [12. s.R] streaking next to the skin.
*Surface of pit cavity.*—Pale yellow [89. p.Y] broken fibers when twisted from stone.
*Amygdalin.*—Scarce.
*Juice.*—Moderate, rich.
*Texture.*—Firm, melting.
*Fibers.*—Abundant, fine.
*Ripens.*—Fairly even.
*Flavor.*—Sub-acid and sweet, typically 15 to 18 brix.
*Aroma.*—Slight.
*Eating quality.*—Very good.

STONE

Type: Clingstone.
Form: Oval.
Hilum: Oblong.
Base: Rounded.
Apex: Acuminate.
Sides: Equal.
Tip: 3/32" [2.4 mm.] long with an angle of 65 to 75 degrees.
Surface: Irregularly furrowed toward the apex, pitted from base beyond the center.
Ridges: Rounded.
External color: Dark orange yellow [72. d.OY].
Pit wall color when cracked: Moderate orange yellow [71. m.OY].
Cavity surface color: Strong yellowish brown [74. s.yBr] with Light yellowish brown [76. l.yBr] blotches.
Average pit wall thickness: 1/4" [6.4 mm.].
Average width: 1 1/16" [27.0 mm.].
Average length: 1 1/2" [38.1 mm.].
Average breadth: 3/4" [19.1 mm.].
Tendency to split: Slight.
Kernel:
*Form.*—Oval.
*Skin color.*—Pale yellow [89. p.Y] when first removed.
*Pellicle color.*—Strong yellowish brown [74. s.y.Br].
*Vein color.*—Strong yellowish brown [74. s.y.Br].
*Taste.*—Bitter.
*Viable.*—Yes.
*Average width.*—1/2" [12.7 mm.].
*Average length.*—3/4" [19.1 mm.].
*Amygdalin.*—Abundant.

Use

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'SPRING CANDY' (U.S. Plant Pat. No. 14,677) peach by producing peaches that are firm in texture, yellow in flesh color, sub-acid in flavor, and mostly red in skin color, but is distinguished therefrom by blooming later, by requiring more chilling hours, and by producing fruit that is clingstone instead of freestone in type, that is sweeter in taste, and that matures about twelve days earlier.

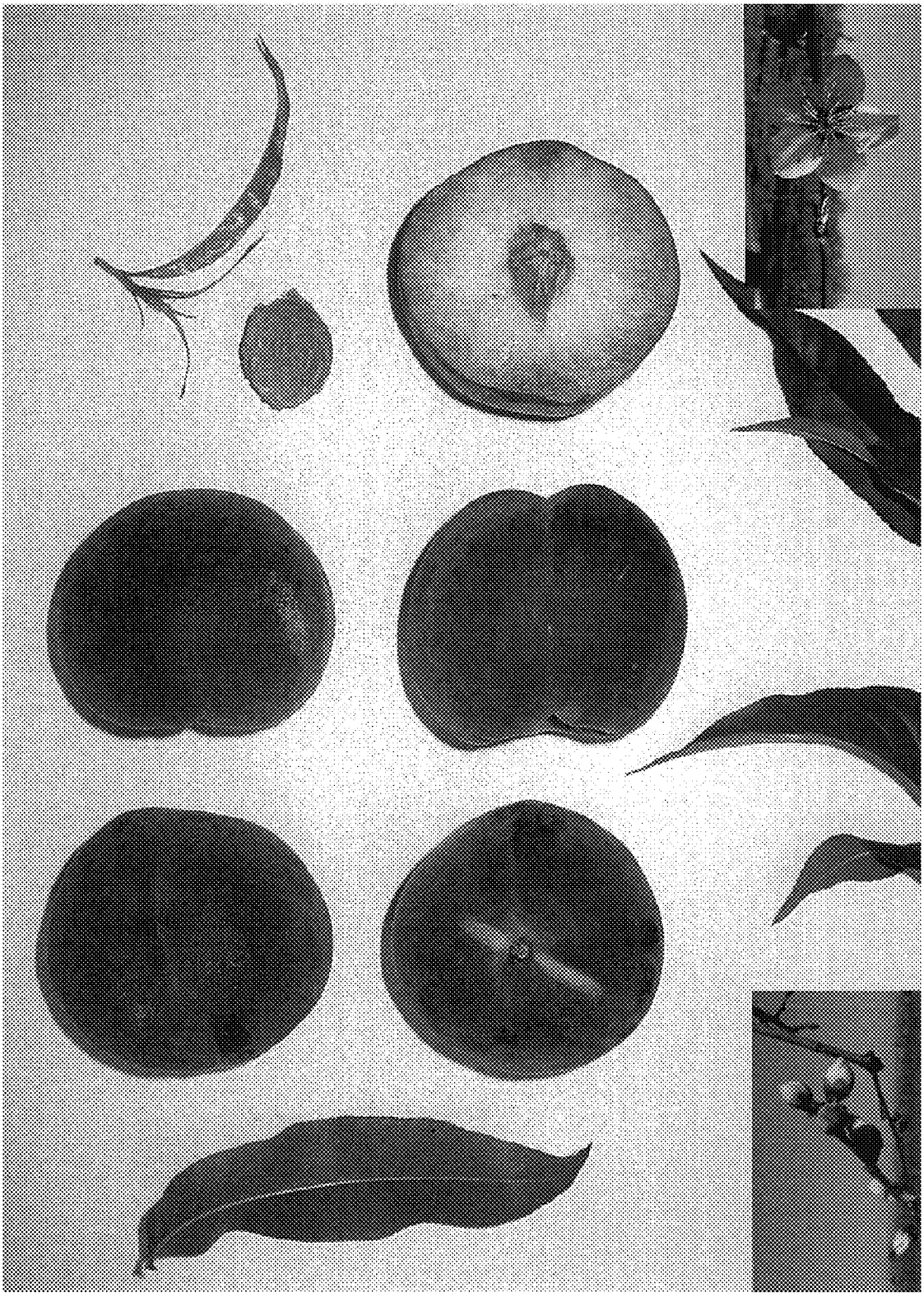

* * * * *